United States Patent
Schnittgrund

(10) Patent No.: US 7,022,415 B2
(45) Date of Patent: Apr. 4, 2006

(54) LAYERED SPHERE BRAZE MATERIAL

(75) Inventor: Gary D. Schnittgrund, Granada Hills, CA (US)

(73) Assignee: Alfred E. Mann Foundation for Scientific Research, Santa Clarita, CA (US)

( * ) Notice: Subject to any disclaimer, the term of this patent is extended or adjusted under 35 U.S.C. 154(b) by 70 days.

(21) Appl. No.: 10/793,457

(22) Filed: Mar. 3, 2004

(65) Prior Publication Data

US 2005/0194425 A1    Sep. 8, 2005

(51) Int. Cl.
*B32B 5/02* (2006.01)
*B32B 5/16* (2006.01)
*B32B 7/04* (2006.01)
*B32B 15/16* (2006.01)
*B23K 1/00* (2006.01)
*B23K 103/08* (2006.01)
*B23K 103/14* (2006.01)
*B23K 103/16* (2006.01)

(52) U.S. Cl. ............... 428/546; 428/614; 428/621; 428/640; 428/661; 428/680; 228/122.1; 228/226; 228/248.5; 228/254; 228/56.3

(58) Field of Classification Search ............... 428/614, 428/621, 640, 661, 680; 228/122.1, 245, 228/246, 248.1, 254, 56.3
See application file for complete search history.

(56) References Cited

U.S. PATENT DOCUMENTS

| | | |
|---|---|---|
| 3,594,895 A | 7/1971 | Hill et al. |
| 3,994,430 A | 11/1976 | Cusano et al. |
| 5,013,612 A | 5/1991 | Hunt et al. |
| 5,028,495 A * | 7/1991 | Hirano et al. ............... 428/622 |
| 6,221,513 B1 | 4/2001 | Lasater |
| 6,521,350 B1 | 2/2003 | Fey et al. |
| 6,722,002 B1 * | 4/2004 | Chang et al. ............... 29/17.2 |
| 2005/0095442 A1 * | 5/2005 | Byers et al. |
| 2005/0103825 A1 * | 5/2005 | Jiang et al. |

* cited by examiner

Primary Examiner—Deborah Jones
Assistant Examiner—Jason L Savage
(74) Attorney, Agent, or Firm—Gary D. Schnittgrund

(57) ABSTRACT

The invention is a method of bonding a ceramic part (6) to a metal part (4) by heating a component assembly (2) comprised of the metal part (4), the ceramic part (6), and a thin laminated interlayer material (8) placed between the two parts and heated at a temperature that is greater than the temperature of the eutectic formed within the laminated interlayer material (8) or between the metal part (4) and the laminated interlayer material (8), but that is less than the melting point of the ceramic part (6) or of the metal part (4). The component assembly (2) is held in intimate contact at temperature in a non-reactive atmosphere for a sufficient time to develop a strong bond between the ceramic part (6) and the metal part (4). The compact interlayer material (8') may be further comprised of two or more sets of metal alloy spheres (16, 16') each having distinct compositions. Further, the compact interlayer material (8') may be formed of composite spheres (19) that are each comprised of laminant layers (18, 40) where each laminant layer has a distinct composition.

7 Claims, 2 Drawing Sheets

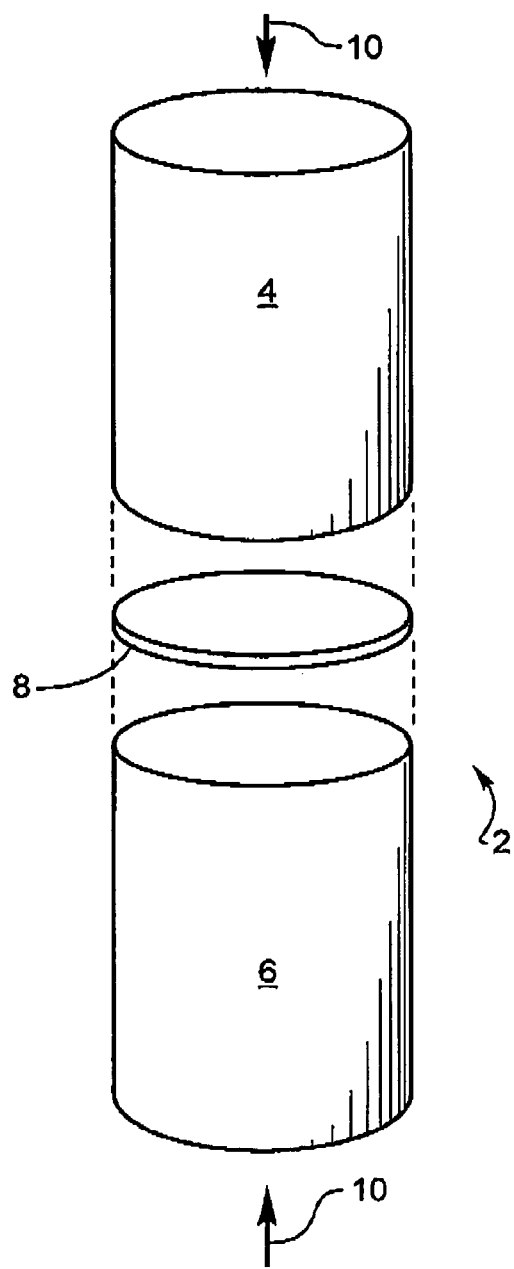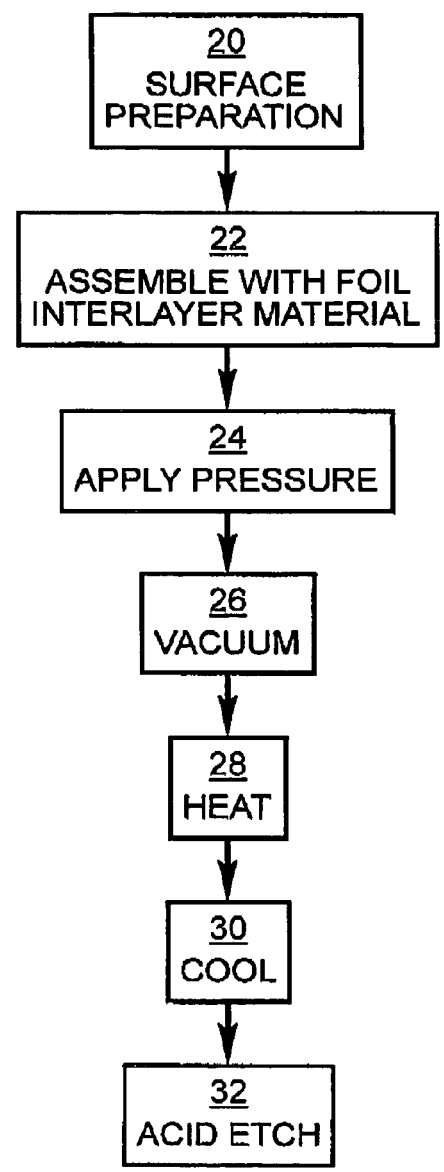

LAYERED SPHERE BRAZE MATERIAL

FIELD OF THE INVENTION

This invention relates to a method of producing a hermetically sealed ceramic to metal bond for implantation in living tissue.

BRIEF DESCRIPTION OF THE DRAWINGS

FIG. 1 illustrates a side view of the component assembly with the laminant interlayer material as a foil between the ceramic and metal parts.

FIG. 2 schematically depicts the bonding steps of the present invention.

DETAILED DESCRIPTION OF THE PREFERRED EMBODIMENT

Figure 3:
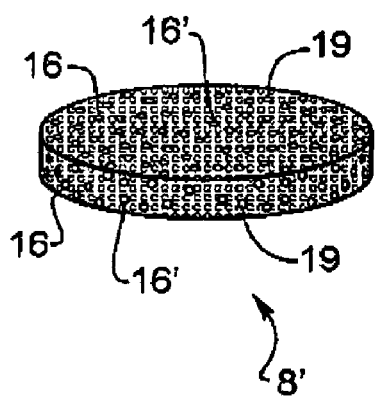
FIG. 3 illustrates the compact interlayer material comprised of material spheres.

FIG. 1 shows component assembly 2 having metal part 4, ceramic part 6, and interlayer material 8. Component assembly 2 is heated to a specific process temperature, that is below the melting point of metal part 4, for a specific period of time, at a pressure that is created by force 10 and that is exerted so as to place laminated interlayer material 8 in intimate contact with the metal and ceramic parts.

Interlayer material 8 comprises a metal foil having a thickness of about five-thousandths of an inch or less. Interlayer material 8 is selected from the group of materials that are compatible with the ceramic chosen for ceramic part 6 in that they wet the surface during the bonding process and enter into a diffusion process with the ceramic part 6 thereby creating a strong bond joint during processing. Interlayer material 8 also is selected from the group of materials that are compatible with the metal chosen for a metal part 4. Interlayer material 8 forms a bond with the metal part 4 by virtue of developing a eutectic alloy at the bonding temperature and pressure utilized during processing. The lowest eutectic temperature, for example, in the nickel-titanium system is about 942° C. at about 28 weight percent nickel and 72 weight percent titanium. The group of interlayer materials includes substantially pure nickel, i.e., pure nickel and nickel containing approximately two percent or less by weight of other alloy metals and substantially pure titanium, i.e., pure titanium and titanium containing approximately two percent or less by weight of other alloy metals.

Metal part 4 may be selected from a group of biocompatible materials, such as a titanium alloy, and is Ti-6Al-4V in a preferred embodiment. Ceramic part 6 may be alumina, titania, zirconia, stabilized-zirconia, partially-stabilized zirconia, tetragonal zirconia, magnesia-stabilized zirconia, ceria-stabilized zirconia, yttria-stabilized zirconia, and calcia-stabilized zirconia, and in a preferred embodiment ceramic part 6 is yttria-stabilized zirconia. In alternative embodiments, rather than using interlayer material 8 as a foil, interlayer material 8 may be a stack of thin coatings that are applied to either the metal part 4 or ceramic part 6 surface to be bonded by any of a variety of chemical processes such as electroless plating and electroplating, or by any of a variety of thermal processes such as sputtering, evaporating, or ion beam enhanced deposition. Interlayer material 8 may be applied as layers of thin coatings of metallic beads or as layers of metallic powders.

The process steps that are employed to create assembly 2 with a strong bond between metal part 4 and ceramic part 6 are schematically represented in FIG. 2. First, the surfaces to be bonded are prepared in step 20 by machining to assure that they will intimately conform to each other during bonding. The surfaces are smoothed and cleaned.

In step 22, component assembly 2 is prepared with interlayer material 8 between metal part 4 and ceramic part 6. In step 24, force 10 is applied to compress interlayer material 8 between metal part 4 and ceramic part 6. Force 10 is sufficient to create intimate contact between the parts. Force 10 is applied to assure that a homogeneous bond is formed between metal part 4 and ceramic part 6, thus creating a hermetic seal between the two parts.

In step 26 the assembly to be heat processed is placed in a furnace in a non reactive atmosphere, which is preferably vacuum, but which can be argon in an alternative embodiment. A vacuum is applied before the furnace is heated to the processing temperature in step 28. A preliminary holding temperature may be used to allow the thermal mass of the parts to achieve equilibrium before proceeding with heating. The process temperature is lower than the melting point of metal part 4, but greater than the temperature of the eutectic formed by metal 4 and interlayer material 8. It is notable that the interlayer material 8 behaves significantly differently from an alloy of nickel-titanium when heated, as in the application of a braze foil. It is well known that an alloy of nickel-titanium will behave according to the phase diagram relationships that exist for that alloy composition or that exist for that same alloy composition that is heated in contact with a nickel body. On the other hand, for example, heating a pure nickel material in contact with a pure titanium material results in at least some liquidus formation at the lowest eutectic temperature, which is about 942° C. (at the eutectic composition of about 28 weight percent nickel and 72 weight percent titanium).

In a preferred embodiment, the vacuum is $10^{-6}$ to $10^{-7}$ torr, to assure that the laminated interlayer material 8 and metal part 4 do not oxidize. Component assembly 2 is held at the selected temperature, which is typically between approximately 942° and 1080° C., for approximately 5 to 20 minutes, while force 10 continues to be exerted on laminated interlayer material 8. The exact time, temperature and pressure are variable with each other so as to achieve a homogeneous and strong bond of metal part 4 with ceramic part 6. For example, in a preferred embodiment, an yttria-stabilized zirconia part bonds to a Ti-6Al-4V part in vacuum at $10^{-6}$ torr at approximately 980° C. for 10 minutes with a pressure of approximately 5 to 20 psi on a laminated foil comprised of at least one commercially pure nickel layer of approximately 0.0007 inches thickness and at least one titanium layer of 0.0013 inches, yielding a 50 weight percent nickel and 50 weight percent mean composition titanium laminated interlayer material 8.

The component assembly 2 is furnace cooled to room temperature in step 30. In optional step 32, component assembly 2 is cleaned by being placed in a bath, after thermal processing is complete, to assure removal of all nickel and nickel salts. This bath is preferably an acid bath that etches the exposed surfaces of component assembly 2. In a preferred embodiment, the bath is nitric acid. Removal of nickel and nickel salts in the bath etch insures that component assembly 2 is biocompatible. Nickel and nickel salts are detrimental to living animal tissue. In a preferred embodiment, however, all of the nickel that is introduced as laminated interlayer material 8 is combined with the titanium and is combined chemically to be unavailable as free nickel or as a nickel salt.

In this embodiment, a compact interlayer material 8', illustrated in FIG. 3, is comprised of a multitude of small particles, preferably uniform spheres, each having a controlled composition. Obviously, there may be more than two sets of spheres having different compositions or morphologies, but these alternatives are not illustrated. It is known that the small particles may have other shapes than spheres and that they may not be uniform in size or shape. Further, the final composition of the compact interlayer material 8' is controlled by total volume of primary alloy particle 16 and secondary alloy particle 16' and as the compact interlayer material 8' has been additionally alloyed by diffusion from metal part 4 and/or ceramic part 6 of FIG. 1. It is preferred that the mean composition of the compact interlayer material 8' be chosen so that depletion of either or any of the materials, nickel or titanium, for example, does not occur during the brazing operation. Preferred mean compositions for compact interlayer material 8' contain about 20 to 70 volume percent of nickel with the balance titanium.

Figure 4:
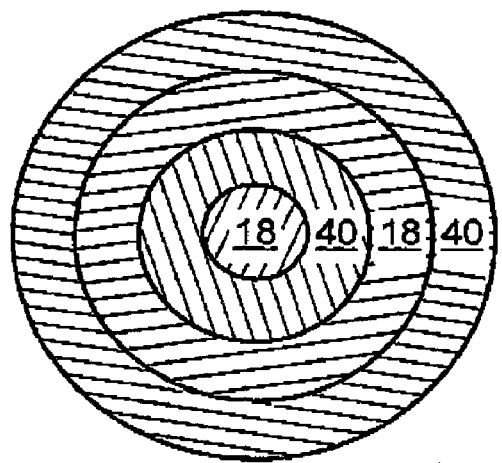
FIG. 4 presents a cross-sectional view of the interlayer material spheres.

In a further alternative embodiment, the primary alloy particle 16 or the secondary alloy particle 16' may be comprised of layered materials, as illustrated by composite particle 19, FIG. 4, wherein the sets of particles, illustrated in FIG. 3, may have different compositions of layered materials. In a preferred embodiment, for example, composite particle 19 presents the cross-sectional view of a layered composite sphere that is comprised of primary particle laminate layer 18, optionally titanium, alternated with secondary particle laminate layer 40, optionally nickel. Compact interlayer material 8' is comprised of a plurality of composite particles 19, wherein the distribution of sizes, morphologies, and shapes is varied to achieve the desired bond between metal part 4 and ceramic part 6 when temperature and optionally pressure are applied.

As previously discussed, but equally applicable to the invention, it is preferred that the mean composition of the compact interlayer material 8' be chosen so that depletion of the material, nickel or titanium, for example, does not occur during the brazing operation. Preferred mean compositions for compact interlayer material 8' contain about 20 to 70 volume percent of nickel with the balance titanium. It is preferred that the mean composition of primary alloy particle 16 of FIG. 4 comply with this compositional guideline. While numerous metals demonstrate formation of eutectic compositions, nickel and titanium are exemplar selections that are useful in an implantable device. Other interesting materials that demonstrate eutectic formation include nickel-titanium, titanium-copper-silver, titanium-copper-nickel, gold-tin, copper-silver, copper-magnesium, copper-titanium, niobium-nickel, nickel-silicon, nickel-zirconium, silver-silicon, silver-tin, silver-titanium, gold-silicon, and gold-titanium.

The layered particles 19 are made by any of a number of known techniques, including aerosol techniques or vapor deposition techniques. In this manner, the total composition of the compact interlayer material is controllable on a macro level as well as on a micro (interparticle) level, thereby aiding densification of the compact interlayer material 8' and the bonding of component assembly 2. It is known to the inventor to vary the composition of the outer layer of the secondary particle laminate layer 40, as illustrated in FIG. 4, to enhance densification and bonding at low temperatures and optionally at low pressures.

Component assembly 2 is preferably biocompatible after bonding and processing. Metal part 4, ceramic part 6, and interlayer material 8 are selected to be compatible with the environment in a living body. Hence, metal part 4 is typically a titanium alloy and ceramic part 6 is typically zirconia.

In a preferred embodiment, component assembly 2 is either an electrical sensor or an electrical stimulator that is implanted in a human body, although it could equally well be implanted in any animal, it must survive long periods in the hostile environment of a living body, which is basically a warm saline solution. In a preferred embodiment, component assembly 2 is either a sensor or stimulator comprised of a hollow ceramic tube that contains various electronic components that is bonded to a metal electrode end. The component assembly is preferably watertight; hence, the bond is hermetic, resisting salt-water intrusion as well as growth of living tissue into the metal-to-ceramic bond joint.

Further, component assembly 2 does not corrode while implanted in the body. The materials are chosen such that post-bonding they are not susceptible to corrosion either individually or in the as-bonded state. Component assembly 2 resists electrolytic corrosion as well as crevice corrosion, because of the materials selected for component assembly 2.

Obviously, many modifications and variations of the present invention are possible in light of the above teachings. It is therefore to be understood that, within the scope of the appended claims, the invention may be practiced otherwise than as specifically described.

What is claimed is:

1. A component assembly (2) for use in living tissue comprising:
    a ceramic part (6);
    a metal part (4); and
    a compact interlayer material (8') comprised of a plurality of metal composite particles (19), each of the metal composite particles (19) is comprised of a primary particle laminate layer (18) and a secondary particle laminate layer (40), each layer comprising a metal selected from the group consisting of metals that form a eutectic composition, for bonding said ceramic part (6) to said metal part (4).

2. The component assembly (2) of claim 1 wherein said primary particle laminate layer (18) is comprised of substantially pure nickel and a secondary particle laminate layer (40) is comprised of substantially pure titanium.

3. The component assembly (2) of claim 1 wherein said metal composite particles (19) have an outer layer that is comprised of substantially pure nickel.

4. The component assembly (2) of claim 1 wherein said primary particle laminate layer (18) is comprised of substantially pure nickel and said secondary particle laminate layer (40) is comprised of an alloy of titanium.

5. The component assembly (2) of claim 1 wherein said metal composite particles (19) are formed in the shape of a sphere.

6. The component assembly (2) of claim 5 wherein said primary particle laminate layer (18) is formed in the shape of a sphere.

7. The component assembly (2) of claim 5 wherein said secondary particle laminate layer (40) is formed in the shape of a sphere.

* * * * *